United States Patent [19]

Gordon et al.

[11] Patent Number: 4,910,978
[45] Date of Patent: Mar. 27, 1990

[54] REUSABLE SOFT FABRIC COLD COMPRESS

[75] Inventors: Tim H. Gordon, Maywood; Stanley Walasek, Bridgewater, both of N.J.; Peter S. Bernard, Bedford, N.Y.

[73] Assignee: Becton, Dickinson and Company, Franklin Lakes, N.J.

[21] Appl. No.: 317,110

[22] Filed: Feb. 28, 1989

Related U.S. Application Data

[63] Continuation of Ser. No. 614,347, May 25, 1984, abandoned.

[51] Int. Cl.⁴ .............................................. F25D 3/08
[52] U.S. Cl. ..................................................... 62/530
[58] Field of Search .......................... 62/530; 165/46; 215/13 R

[56] References Cited

U.S. PATENT DOCUMENTS

| | | | |
|---|---|---|---|
| 1,576,488 | 3/1926 | Hodgson | 62/530 X |
| 2,563,933 | 8/1951 | Hipps et al. | 62/530 X |
| 2,595,328 | 5/1952 | Bowen | 62/530 |
| 3,885,403 | 5/1975 | Spencer | 62/530 |
| 4,114,620 | 9/1978 | Moore et al. | 128/254 |
| 4,324,111 | 4/1982 | Edwards | 62/530 X |
| 4,344,303 | 8/1982 | Kelly, Jr. | 62/530 |
| 4,356,709 | 11/1982 | Alexander | 62/530 |
| 4,381,025 | 4/1983 | Schooley | 150/2.4 |
| 4,399,668 | 8/1983 | Williamson | 62/530 X |
| 4,404,820 | 9/1983 | Romaine | 62/530 |
| 4,462,224 | 7/1984 | Dunshee et al. | 62/530 |

FOREIGN PATENT DOCUMENTS 1383536  2/1975  United Kingdom .

Primary Examiner—Lloyd L. King
Attorney, Agent, or Firm—John L. Voellmicke

[57] ABSTRACT

A reusable compress for cold therapy includes a flexible pack containing a gel wherein the pack and the gel are capable of remaining flexible to a low temperature of about −18° C. The pack includes a patient contact portion for conforming to variations in surface contour of the patient's body. This patient contact portion includes an inner plastic layer, having a thickness of up to about 3.0 mils, in contact with the gel and an outer patient contacting fabric layer laminated to the plastic layer. The combined strength of the laminated structure is sufficient to contain the gel during normal use.

3 Claims, 4 Drawing Sheets

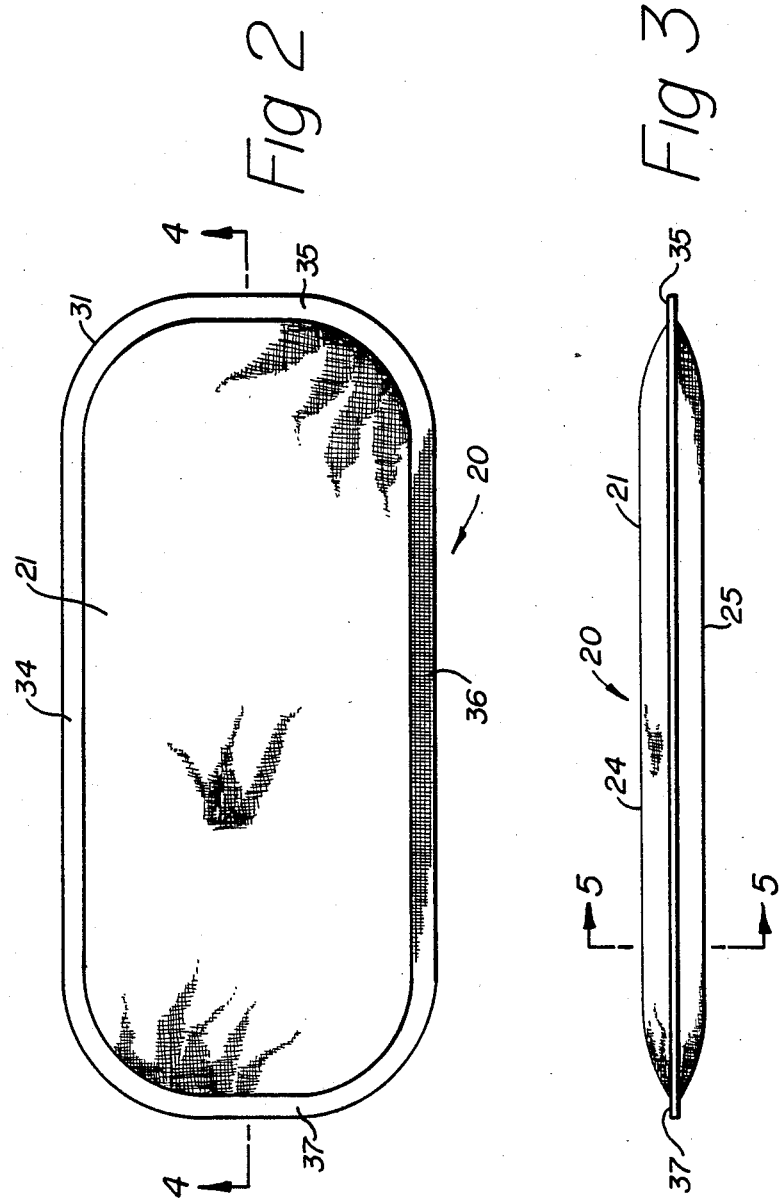

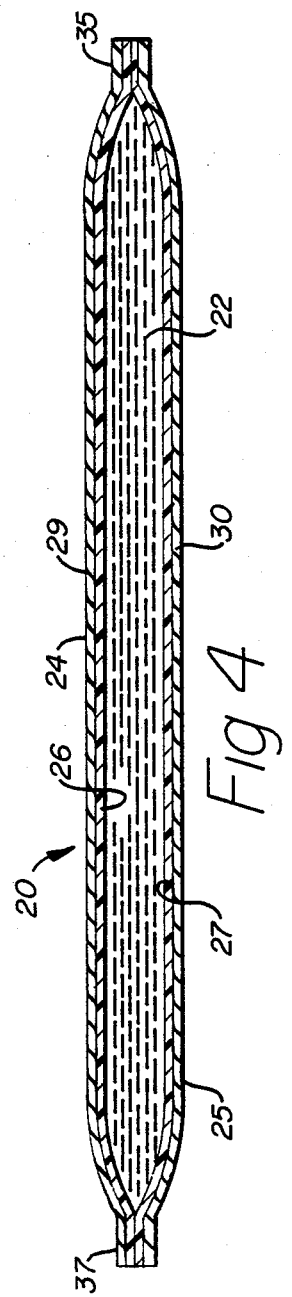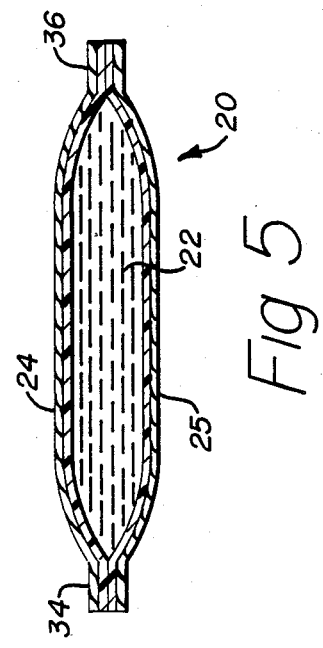

REUSABLE SOFT FABRIC COLD COMPRESS

This application is a continuation of application Ser. No. 614,347, filed May 25, 1984 now abandoned.

FIELD OF THE INVENTION

The present invention relates to a therapeutic compress and more particularly concerns a reusable soft fabric cold compress for application of cold therapy.

DESCRIPTION OF THE PRIOR ART

Cold therapy is a recommended treatment, particularly when the limb of a person has been injured. For many years this therapy was provided via an ice bag which was held against the injured portion of the limb. In recent years, improved products have been developed for use in providing cold therapy.

Known reusable cold packs consist of a gel material contained within a plastic envelope which will remain flexible when refrigerated. In use, the refrigerated cold pack is placed against that portion of the patient's body requiring therapy. When the pack becomes warm due to exposure to the patient and the environment, it may be re-refrigerated and used again. The cold pack with a gel is an improvement over the ice bag because it is easier to use repeatedly and because its flexibility provides better heat transfer by conforming more closely to the patient's body than the rigid ice cubes. The envelope containing the gel is made flexible so that it will conform to the contour of the patient's body. However, this flexibility requirement is compromised because the pack must also be thick and tough enough to withstand repeated usage. Such a cold pack containing a refrigeratable gel is taught in U.S. Pat. No. 3,885,403 to Spencer.

Known refrigeratable cold packs have shortcomings in that the surface of a cold plastic envelope collects moisture which condenses from the atmosphere. This moisture is uncomfortable to the user. Further, the cold plastic envelope has a very uncomfortable feel and the cold surface could become painful to the patient so that periodic removal of the cold pack is required.

Fabric covers for cold packs are also known in the art. These covers, such as taught in U.S. Pat. No. 4,381,025 to Schooley, keep the portion of the patient's body adjacent to the cold pack dry, and they provide a more comfortable surface for patient contact. Moore et al., U.S. Pat. No. 4,114,620, teach a plastic pad with passages for circulating hot or cold water to provide hot or cold therapy. Moore et al. teach the attaching of cellulosic fibers directly to the plastic film to form a patient contact panel to provide a highly liquid absorptive surface for moist therapy and further to provide a soft feel. Turner, in U.K. Patent No. 1,383,536, teaches a non-reusable hot or cold pack wherein the pack is made hot or cold via an exothermic or endothermic reaction, respectively, initiated by rupturing an internal membrane which separates the chemicals of the reaction. Turner further teaches an outer layer, on the pack, having lower thermal conductivity to prolong the life of the pack by reducing the rate of heat transfer. Turner also teaches that this layer improves the feel qualities of the pack and eliminates the discomfort caused by moisture condensation.

Various solutions for improving comfort and absorbing moisture on the surface of plastic hot or cold therapy products have been addressed by the prior art, some of which have been mentioned above. There is still, however, a need for a simple, straightforward, easily fabricated, reusable refrigeratable cold compress which has a soft compliant outer surface that will conform to variations in the surface contour of the patient's body but will be strong and tough enough to withstand repeated usages and still provide a comfortable dry feel to the patient.

SUMMARY OF THE INVENTION

The compress for cold therapy of the present invention includes a flexible pack containing a fluid wherein the pack and the fluid are capable of remaining flexible after being refrigerated. The pack includes a patient contact portion for conforming to variations in surface contour of the patient's body. This contact portion includes an inner plastic layer laminated to an outer patient contacting fabric layer. The inner plastic layer is in contact with the fluid and preferably has a thickness of up to about 3.0 mils. The combined strength of the laminated structure of the plastic layer and the fabric layer is sufficient to contain the fluid during normal use.

In another embodiment of the present invention, a reusable refrigeratable cold compress includes a flexible pack containing a refrigeratable gel wherein the pack add the gel are capable of remaining flexible to a low temperature of about $-18°$ C. The pack includes a patient contact portion for conforming to variations in the surface contour of the patient's body. This contact portion includes an inner plastic layer laminated to an outer patient contacting fabric layer. The inner plastic layer is in contact with the gel and has a thickness of up to about 3.0 mils. The combined strength of the laminated structure of the plastic layer and the fabric layer is sufficient to contain the gel during normal use.

In accordance with the preferred embodiment of the present invention, a reusable refrigeratable soft fabric cold compress includes a flexible pack containing a refrigeratable gel wherein the pack and the gel are capable of remaining flexible to a low temperature of about $-18°$ C. The pack includes an inner vinyl layer in contact with the gel and an outer patient contacting fabric layer laminated to the inner vinyl layer. The inner vinyl layer has a thickness of up to about 5.0 mils. This compress is non-freestanding at a temperature of about $+21°$ C. and is capable of conforming to variations in the surface contour of he patient's body. The combined strength of the laminated structure of the vinyl layer and the fabric layer is sufficient to contain the gel during norma use.

BRIEF DESCRIPTION OF THE DRAWINGS

FIG. 2 is a top plan view of the preferred reusable refrigeratable soft fabric cold compress;

FIG. 3 is a side elevation view of the preferred reusable refrigeratable soft fabric col compress;

FIG. 4 is a cross-sectional view of the cold compress of FIG. 2 taken along line 4—4;

FIG. 5 is a cross-sectional view of the cold compress of FIG. 3 taken along line 5—5.

DETAILED DESCRIPTION

Figure 1:
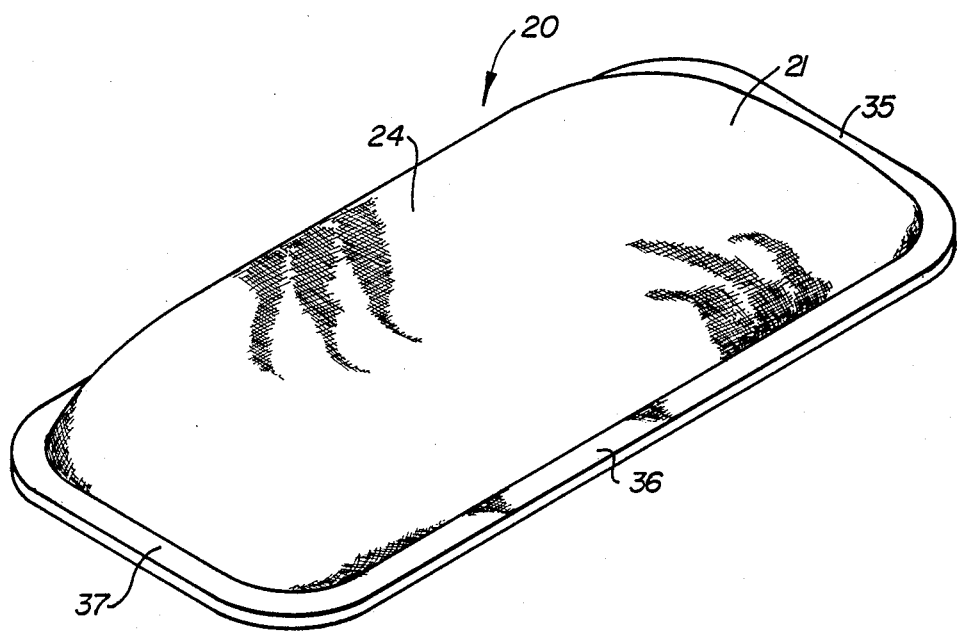
FIG. 1 is a perspective view of the preferred reusable refrigeratable soft fabric cold compress of the present invention.

While this invention is satisfied by embodiments in many different forms, there is shown in the drawings and will herein be described in detail preferred embodiments of the invention with the understanding that the present disclosure is to be considered as exemplary of the principles of the invention and is not intended to limit the invention to the embodiments illustrated. The scope of the invention will be measured by the appended claims and their equivalents.

Adverting now to FIGS. 1 through 5, a reusable refrigeratable soft fabric cold compress 20 includes a flexible pack 21 containing a refrigeratable gel 22. Both the pack and the gel are soft and flexible to a low temperature of about −18° C. Although a gel is preferred, other fluids that remain flexible after being refrigerated, such as water, may be used. Also, the lower the temperature the fluid r gel can be reduced to, while remaining flexible, the more heat energy it will absorb during therapy. Accordingly, a fluid or gel that remains flexible to a low temperature of about −18° C. is preferred.

The pack has a first side 24 and a second side 25. Both sides are made of a lamination of plastic film 26 and 27, respectively, and knitted or woven fabric layer 9 and 30, respectively. The sides are oriented so that plastic film layer 26 of the first side contacts plastic film layer 27 of the second side. Sides 24 and 25 are joined together around their periphery 31 by heat sealing, ultrasonic welding, RF (radio frequency) welding or other suitable means to form sealed edges 34,35,36 and 37. RF welding is preferred wherein sides 24 and 25 are held firmly together, at their respective outside edges, with a portion of their plastic film layers 26 and 27 in contact with each other so that the radio frequency energy, when applied, melts the adjacent portions of plastic film 26 and 27 creating a sealing weld which joins the films in an airtight arrangement. It is preferred that three of the edges, for example, edges 34,35 and 36, are sealed first to form a receptacle into which an appropriate amount of gel 22 is deposited. Edge 37 is then sealed shut, thus forming an enclosed bladder to contain the gel. In one embodiment of the preferred fabric compress, the first and second sides are approximately 5 inches (2.0 cm) long by 11 inches (4.3 cm) wide. Sides of this size form a compress of convenient size for use on many common injuries such as sprained ankles and knees of human patients as well as some animals.

It will be apparent to one skilled in the art that numerous constructions can be used to join the laminated sides of the soft fabric compress of the present invention and that the arrangement described herein is exemplary of these many possibilities. Also, it is within the purview of this invention to include a one-piece compress wherein the sides are formed of one laminated sheet folded over upon itself so that one of the edges is formed by a fold in the laminated sheet material and, accordingly, requires no sealing operation.

Known reusable plastic wall compresses are made of vinyl film in the range of 8–11 mils thick and of other plastic films, such as polyethylene, in the range of 4–6 mils. Vinyl film, formulated to be flexible when used at low temperatures, such as −31° C., has less strength than many other films. Also, it is difficult to manufacture thin vinyl film, less than about 5 mils thick, that is uniformly free of small holes and other imperfections that would compromise its use in a liquid container. Therefore, thicker vinyl film is used in the known compresses. These plastic materials are strong enough to withstand repeated usages, but the resulting compresses are relatively rigid and usually freestanding. As used herein, freestanding means that, at a temperature of about +21° C., if a rectangularly shaped planar compress is positioned perpendicularly on a flat surface, so that one of its long edges contacts the surface, and it is bent slightly to prevent it from toppling over, the compress would tend to remain in that position. However, a non-freestanding compress in the above-described position, would collapse under its own weight. Also, the known compresses neither provide a good feel to the patient nor do they easily conform to the contours of the patient's body. Further, the cold plastic film forms a surface for condensation of moisture from the air which is not comfortable to the patient. A compress having thinner plastic walls would be an improvement because it would be more compliant and non-freestanding. However, it is believed that thinner plastic materials, used alone without a composite structure which includes a fabric, would not be durable enough to contain the gel against the thermal and physical stresses of long term repeated usage of the product. In addition, the plastic material is still cold to the touch.

Plastic film 26 and 27 should be as thin as possible. Vinyl film from 2.0 to 5.0 mils thick is desirable with 4.0 mils thick vinyl film being preferred. Other plastic films, such as polyethylene and polyurethane, from 1.0 to 3.0 mils thick are desirable with 3.0 mils thick polyurethane being preferred. In the preferred embodiment of the present invention, the sides of the pack are made of 4 mil vinyl laminated to an interlock knit, 70 denier, 28 gauge, 4.25–4.50 square yards per pound polyester fabric. The resulting compress, when compared to thicker, all plastic wall compresses, is softer, more compliant and non-freestanding. Also, small holes or other imperfections that may be contained in the vinyl can be sealed by using a laminating process which uses adhesive, wherein the adhesive blocks these holes or imperfections. Further, the vinyl film in the preferred compress, strengthened by the knitted polyester laminate, provides a gel containing pack which is strong enough to withstand repeated usages without gel leakage while providing the flexibility and conformity of a pack made of thinner material. The composite structure of laminated vinyl and knitted polyester provides an exterior surface which is soft and comfortable to the touch and provides a dry feel to the patient.

It will be apparent to one skilled in the art that numerous compress shapes may be used for effective cold therapy and that the preferred rectangular shape described herein is exemplary of these many possibilities. It is within the purview of this invention to include glove or pocket shaped cold therapy products wherein one or both sides of the glove or pocket is constructed of the cold compress of the present invention.

Figure 6:
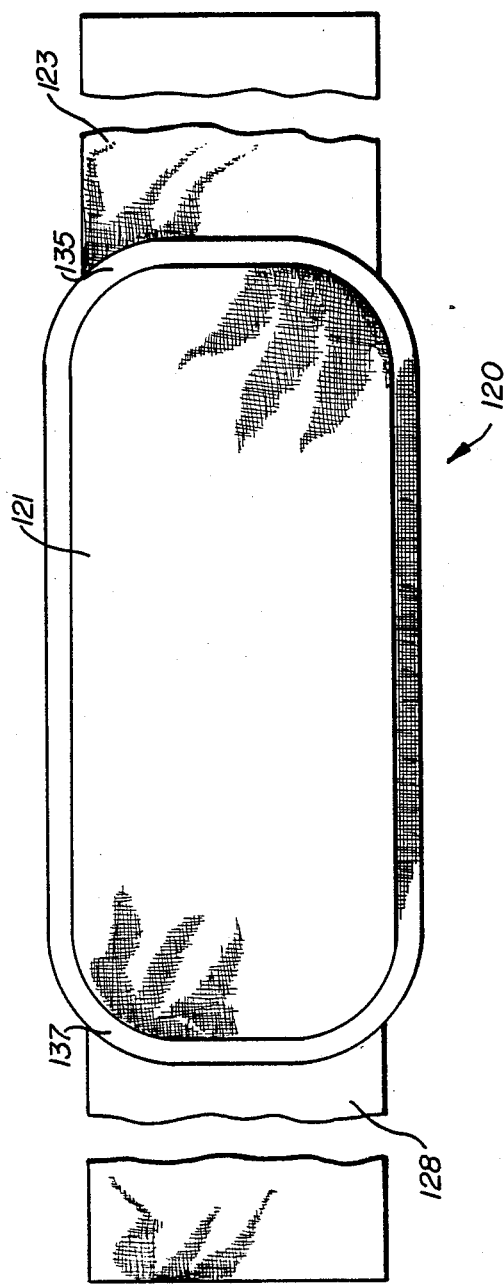
FIG. 6 is a top plan view of an alternative embodiment of the present reusable refrigeratable soft fabric cold compress.

Turning to FIG. 6, an alternative embodiment of the present reusable refrigeratable soft fabric cold compress 120 is shown. This alternative compress includes a flexible pack 121 containing a refrigeratable gel (not shown) and bandages 123 and 128 made of elongated strips of preferably elastic material attached to edges 135 and 137, respectively, of the flexible pack. The bandages are used to hold the cold compress against the portion of the patient's body requiring cold therapy. Bandages 123 and 128 are preferably significantly longer in the longitudinal direction than in width so that they may be properly wrapped around a portion of the patient's body. The elastic material is preferably fabricated with elastic stretch yarns which are interwoven into the material. One such material which may be used for the present embodiment is the ACE® brand elastic bandage (ACE is a registered trademark of Becton, Dickinson and Company, Paramus, N.J.).

A wide variety of plastic films are suitable for the plastic film layer of the compress sides with vinyl, having a thickness of about 4 mils, and polyurethane or polyethylene, having a thickness up to about 3.0 mils, being preferred. Knitted, woven, or non-woven, synthetic or natural fabrics, which are capable of being laminated to the plastic film, are suitable for the fabric layer of the compress sides with knitted, 40–150 denier, 18–36 gauge, 2.3–5.5 square yards per pound polyester fabric being desirable and 70 denier, 28 gauge, 4.25–4.50 square yards per pound, heatset and framed polyester fabric being preferred. It should be noted that the fabric chosen should provide additional strength to the laminated structure in all directions in the plane of the fabric. Accordingly, fabrics which exhibit very low strength in one direction or, as in the case of some non-woven fabrics, in all directions, are not generally suitable for use as the fabric layer. However, fabrics which exhibit weakness in one direction ma be laminated together in multiple layers wherein the weak direction in each fabric layer runs transversely to the weak direction in the adjacent fabric layer thus producing a multilayer fabric, having more uniform strength properties, that is suitable for use in the present invention.

Refrigeratable and heatable gels are known in the art. The gel used in the present invention should remain flexible at low temperatures to −18° C. or even lower. Like the sides of the flexible pack, the gel contained therein should remain flexible after refrigeration so that it will conform to the surface contour of the patient's body during use of the cold compress. In the preferred embodiment of the invention, the gel includes about 73 to 77 weight percent distilled water, 22–24 weight percent freezing point suppressant, preferably propylene glycol, and 1 to 2 weight percent of thickening agent such as Carbopol 940, acrylic acid polymer powder, manufactured by The B. F. Goodrich Company. Ingredients to suppress bacterial growth within the gel and to enhance processibility and/or shelf life may be added.

In preparation for use, the preferred reusable soft fabric cold compress is placed in a refrigerator or a freezer to reduce the temperature of the cold compress. In a typical household freezer, the temperature is about −12° C. In the event of an injury requiring cold therapy, the preferred soft fabric cold compress is removed from the refrigerator or freezer and manually held against that portion of the patient's body requiring cold therapy. The flexibility and non-freestanding properties of the preferred compress allow it to conform to the contour of the patient's body to thereby impart efficient and effective therapeutic treatment. The preferred cold compress may also be held against the patient's body using an elastic bandage. When the preferred soft fabric cold compress loses its coolth due to exposure to the patient and the enviroment, it should be replaced by another refrigerated soft fabric cold compress, if the therapy is to continue uninterrupted. The soft exterior fabric is comfortable to the patient, and moisture is not felt by the patient. The used soft fabric cold compress may be returned to the refrigerator or freezer to reduce its temperature and prepare it for the next use.

In using the alternative embodiment of the preferred soft fabric cold compress, illustrated in FIG. 6, the cold compress is held in place by wrapping elastic strips 123 and 128 around that portion of the patient's body which is in contact with the cold compress. Again, after use the cold compress is returned to the refrigerator or freezer to prepare it for the next use.

Thus, the present invention provides a simple, straightforward, easily fabricated, reusable refrigeratable cold compress which has a soft compliant outer surface that conforms to variations in the surface contour of the patient's body, but is strong and tough enough to withstand repeated usages and still provide a comfortable dry feel to the patient.

What is claimed is:

1. A reusable refrigeratable soft fabric cold compress comprising:
    a flexible pack containing a refrigeratable gel, said pack and said gel capable of remaining flexible to a low temperature of about −18° C., said pack including an inner plastic layer in contact with said gel and an outer patient contacting fabric layer laminated to said inner plastic layer, said inner plastic layer having a thickness of up to about 3.0 mils, said compress being non-freestanding at a temperature of about +21° C. and capable of conforming to variations in surface contour of the patient's body, the combined strength of the laminated structure of said plastic layer and said fabric layer being sufficient to contain said gel during normal use; and
    said gel includes about 73 to 77 weight percent of water, 22 to 24 weight percent of freezing point suppressant and about one to two weight percent of thickening agent.

2. A reusuable refrigeratable soft fabric cold compress comprising:
    a flexible pack containing a refrigeratable gel, said pack and said gel capable of remaining flexible to a low temperature of about −18° C., said pack including an inner vinyl layer in contact with said gel and an outer patient contacting fabric layer laminated to said inner vinyl layer, said inner vinyl layer having a thickness of up to about 5.0 mils, said fabric layer being made of knitted polyester fabric, said compress being non-freestanding at a temperature of about +21° C. and capable of conforming to variations in surface contour of the patient's body, the combined strength of the laminated structure of said vinyl layer and said fabric layer being sufficient to contain said gel during normal use; and
    said gel including about 73 to 77 weight percent of water, about 22 to 24 weight percent of freezing point suppressant and about one to two weight percent of thickening agent.

3. A reusuable refrigeratable soft fabric cold compress comprising:
    a flexible pack containing a refrigeratable gel, said pack and said gel capable of remaining flexible to a low temperature of about −18° C., said pack including an inner vinyl layer in contact with said gel and an outer patient contacting fabric layer laminated to said inner vinyl layer, said inner vinyl layer having a thickness of up to about 5.0 mils, said compress being non-freestanding at a temperature of about +21° C. and capable of conforming to variations in surface contour of the patient's body, the combined strength of the laminated structure of said vinyl layer and said fabric layer being sufficient to contain said gel during normal use; and said gel including about 73 to 77 weight percent of water, about 22 to 24 weight percent of freezing point suppressant an about one to two weight percent of thickening agent.

* * * * *